(12) United States Patent
Heath et al.

(10) Patent No.: US 8,192,200 B1
(45) Date of Patent: Jun. 5, 2012

(54) ENDODONTIC APPARATUS AND METHOD

(75) Inventors: Derek E. Heath, Vero Beach, FL (US); Steve Treadway, Johnson City, TN (US)

(73) Assignee: D&S Dental, LLC, Johnson City, TN (US)

( * ) Notice: Subject to any disclaimer, the term of this patent is extended or adjusted under 35 U.S.C. 154(b) by 197 days.

(21) Appl. No.: 12/840,877

(22) Filed: Jul. 21, 2010

Related U.S. Application Data

(60) Provisional application No. 61/227,914, filed on Jul. 23, 2009.

(51) Int. Cl.
*A61C 5/02* (2006.01)

(52) U.S. Cl. .......................................... 433/224; 433/102

(58) Field of Classification Search .................. 433/102, 433/224, 225
See application file for complete search history.

(56) References Cited

U.S. PATENT DOCUMENTS

| | | | |
|---|---|---|---|
| 3,534,476 A | 10/1970 | Winters | |
| 4,268,251 A | 5/1981 | Takasugi et al. | |
| 4,299,571 A * | 11/1981 | McSpadden | 433/102 |
| 4,332,561 A * | 6/1982 | McSpadden | 433/102 |
| 4,824,369 A | 4/1989 | Levy | |
| 5,516,287 A | 5/1996 | Zdarsky | |
| 6,106,296 A | 8/2000 | Johnson | |
| 6,213,771 B1 * | 4/2001 | Fischer | 433/75 |
| 6,217,335 B1 * | 4/2001 | Riitano et al. | 433/224 |
| 6,520,773 B1 * | 2/2003 | Weber | 433/27 |
| 7,226,289 B2 | 6/2007 | Bills | |
| 2005/0282108 A1 * | 12/2005 | Goodis | 433/102 |
| 2006/0110703 A1 * | 5/2006 | Bills | 433/102 |
| 2006/0110704 A1 * | 5/2006 | Bills | 433/102 |
| 2007/0009850 A1 * | 1/2007 | Riitano | 433/102 |
| 2007/0031783 A1 | 2/2007 | Cantatore et al. | |
| 2007/0099149 A1 * | 5/2007 | Levy et al. | 433/102 |

OTHER PUBLICATIONS

Endodontics with MICRO-MEGA, Jan. 2007.

* cited by examiner

*Primary Examiner* — Todd Manahan
*Assistant Examiner* — Michael R Ballinger
(74) *Attorney, Agent, or Firm* — Luedeka Neely Group, PC

(57) ABSTRACT

A method and instrument for removing material from an internal portion of a tooth wherein the tool used to remove the material includes an elongate shaft extending from a first end to a second end; a cutting surface extending along a working portion of the elongate shaft; a handle attached to the first end of the elongate shaft, the handle including a first end and a second end; a projection attached to the elongate shaft and extending around a portion of the perimeter of the shaft substantially adjacent to the first end of the handle, wherein the projection provides a barrier to prevent a user's fingers from moving beyond the handle directly onto the elongate shaft.

6 Claims, 5 Drawing Sheets

ENDODONTIC APPARATUS AND METHOD

CROSS-REFERENCE(S) TO RELATED APPLICATION(S)

This utility patent application claims priority to U.S. Provisional Application Ser. No. 61/227,914 to Heath et al. entitled "Universal Handle for Endodontic Instrument" which was filed on Jul. 23, 2009, the content of which is incorporated herein by reference in its entirety.

FIELD

This disclosure relates to the field of endodontic instruments. More particularly, this disclosure relates to products and methods involving a universal handle for endodontic instruments.

BACKGROUND

In the field of endodontics, one of the most important and delicate procedures is that of cleaning or extirpating a diseased root canal to provide a properly dimensioned cavity while essentially maintaining the central axis of the canal for filling of the canal void and capping of the tooth. When done properly, this step enables substantially complete filling of the canal with biologically inert or restorative material without entrapping noxious tissue in the canal that could lead to failure of the therapy.

In a root canal procedure, the dentist removes diseased tissue and debris from the canal prior to filling the canal with a biologically inert or restorative filling material. In performing this procedure, the dentist must gain access to the entire canal, shaping it as appropriate. Many tools have been designed to perform the difficult task of cleaning and shaping root canals. Historically, dentists have used endodontic instruments, such as files, to remove the soft and hard material from within and adjacent the root canal area. These endodontic instruments are typically tapered rods with helical cutting edges on a working portion generally adjacent a distal end of the rod. The proximal end of the rod typically includes a handle which is adapted to be gripped by a user or by a hand-held device. The user or hand-held device rotates the endodontic instrument within the root canal, wherein the helical cutting surfaces remove material from the walls of the root canal as the file is rotated.

Due to the delicate nature of endodontic procedures, minor variations of movement of an instrument by a dentist may have substantial effects on a patient and the success of a given operation. More substantial movements by a dentist such as, for example, a slip of the thumb and index finger, could cause irreparable damage to a tooth or mouth structure. Ultimately, the more predictable a particular sized endodontic instrument is to a dentist, the less likely such dentist will make errors during an endodontic procedure using the familiar instrument.

Additionally, use of hand-held automated devices to rotate endodontic instruments, while often more efficient, can sometimes limit the ability of a dentist to perform the most detailed portions of a root canal procedure. This is at least partly due to the lack of tactile feedback that is present during root canal procedures in which instruments are manually rotated. Accordingly, dentists sometimes interchange between manual and device rotated instruments during a root canal procedure, which requires duplicative instruments, one set for manual use and one set for use in a device. It would be preferable for a single set of instruments to be usable manually and in a hand-held device.

What is needed therefore is a universal endodontic instrument that may be used by hand or used with a dental rotation device. Moreover, what is needed is a safety barrier to prevent a dentist's thumb and/or finger(s) from slipping on the handle of an endodontic instrument.

SUMMARY

These and other needs a met by a specifically designed endodontic instrument for removing material from an internal portion of a tooth. The instrument includes an elongate shaft, the elongate shaft including a proximal end and a distal end; a cutting surface extending along a working portion of the elongate shaft; a handle attached adjacent the proximal end of the elongate shaft, the handle including a first end and a second end; a projection attached adjacent the elongate shaft and extending around a portion of the perimeter of the shaft substantially adjacent the first end of the handle, wherein the projection provides a barrier to prevent a user's fingers from moving beyond the handle directly onto the elongate shaft. Preferably, the to instrument may be used by hand or may be removably attached to a dental rotation device and used with the rotation device. In a preferred embodiment, the instrument includes a movable stop located around the elongate shaft. The instrument may, for example, include a file, a reamer, or a broach. In a preferred embodiment, at least a portion of the elongate shaft is tapered.

In another aspect, the disclosure includes a method for removing material from an internal portion of a tooth using an embodiment of the endodontic instrument described above, the method including the step of manipulating the endodontic instrument so that material from an internal portion of a tooth is displaced. In a related embodiment, the method includes an additional step of drilling into a tooth to gain access to an internal portion of a tooth. In an alternative embodiment, the step of manipulating further includes an additional step of filling an internal portion of a tooth with a substantially biologically inert substance. In yet another embodiment, all three of the steps including the step of drilling into a tooth, manipulating the endodontic instrument, and filling an internal portion of a tooth are performed. Preferably, the step of manipulating the endodontic instrument may be optionally performed by hand or with the use of a dental rotating device.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Figure 1:
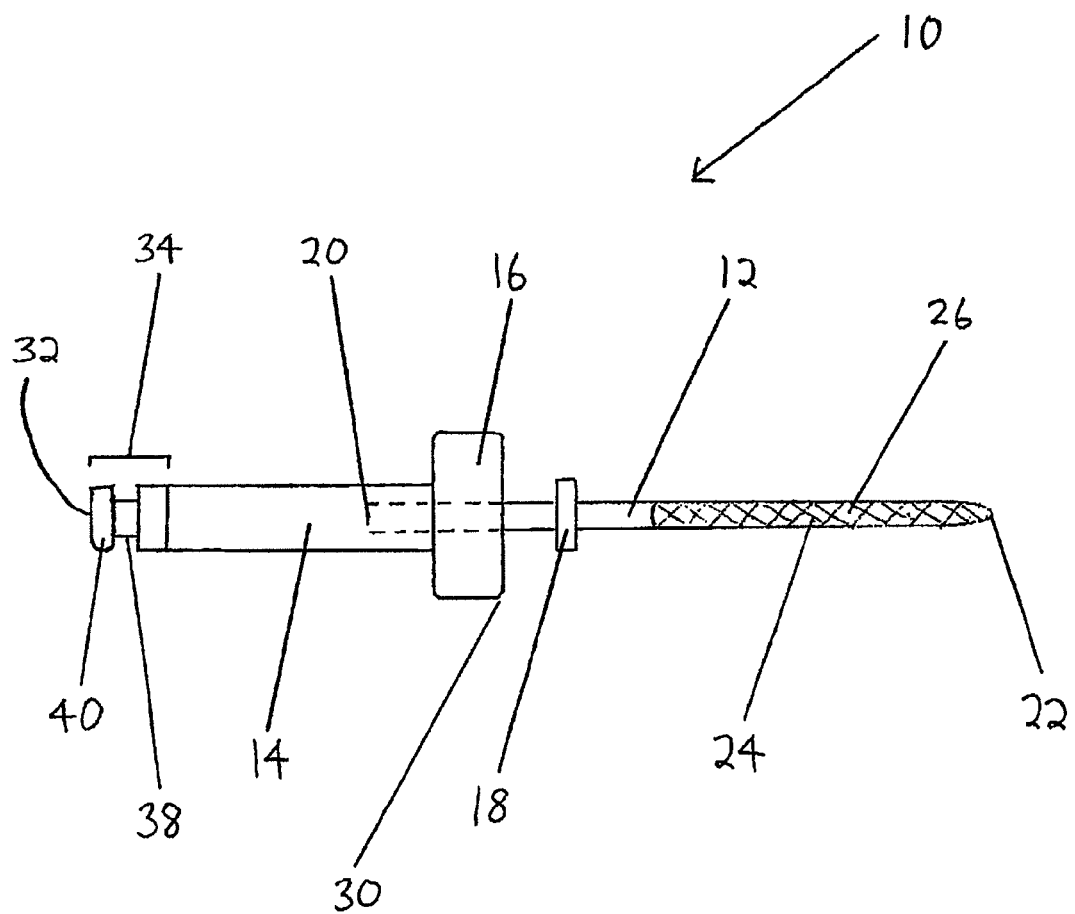
FIG. 1 shows a side view of an embodiment of an endodontic instrument as described herein.

FIG. 1 shows a side view of an endodontic instrument 10 including an elongate shaft 12, a handle 14, and a projection 16. Various embodiments of instrument 10 may include, among other things, a file, a reamer, or a broach. In the embodiment shown in FIG. 1, the instrument 10 further includes a stop 18 that is preferably movably attached along the shaft 12. The stop 18 is preferably made from rubber, plastic, and/or other like substances known to a person having ordinary skill in the art.

The shaft 12 includes a proximal end 20 and a distal end 22. The proximal end 20 of the shaft 12 is attached to and preferably unitary with the handle 14. The embodiment shown in to FIG. 1 includes a shaft 12 including a cutting surface 24 along a working portion 26 of the shaft 12. The shaft 12 typically has a length ranging from about 1.5 centimeters (cm) to about 3 cm, although the present disclosure is usable with shafts of various lengths (e.g., from about 0.1 cm to about 5 cm). The shaft 12 is preferably made of metal or a metal alloy material, which is preferably substantially flexible. Examples of preferred materials for manufacture of the shaft 12 include, for example, stainless steel and nickel titanium ("NiTi") (ranging from about 50/50 by weight, most preferably about 55/45 by weight). The shaft 12 or at least a portion of the shaft 12 is preferably tapered at an angle θ as shown by shaft 28 in the embodiment of an instrument 11 shown in FIG. 2. The angle θ preferably ranges from about 0.5 degrees to about 6 degrees. However, in alternate embodiments, the shaft or a portion thereof may be non-tapered.

Figure 2:
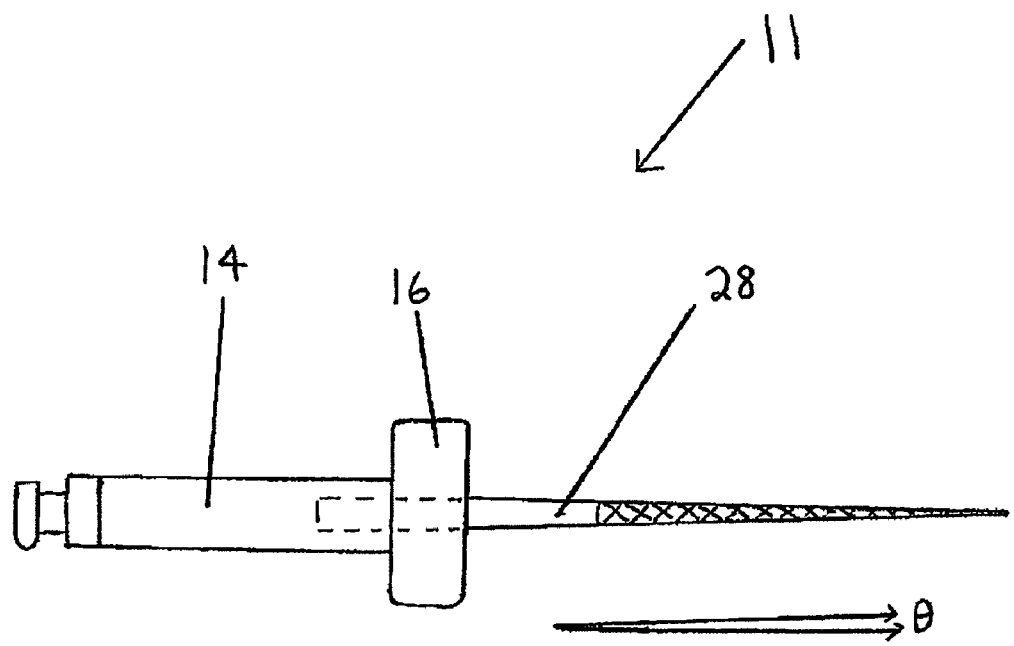
FIG. 2 shows a side view of another embodiment of an endodontic instrument as described herein.
Figure 3:
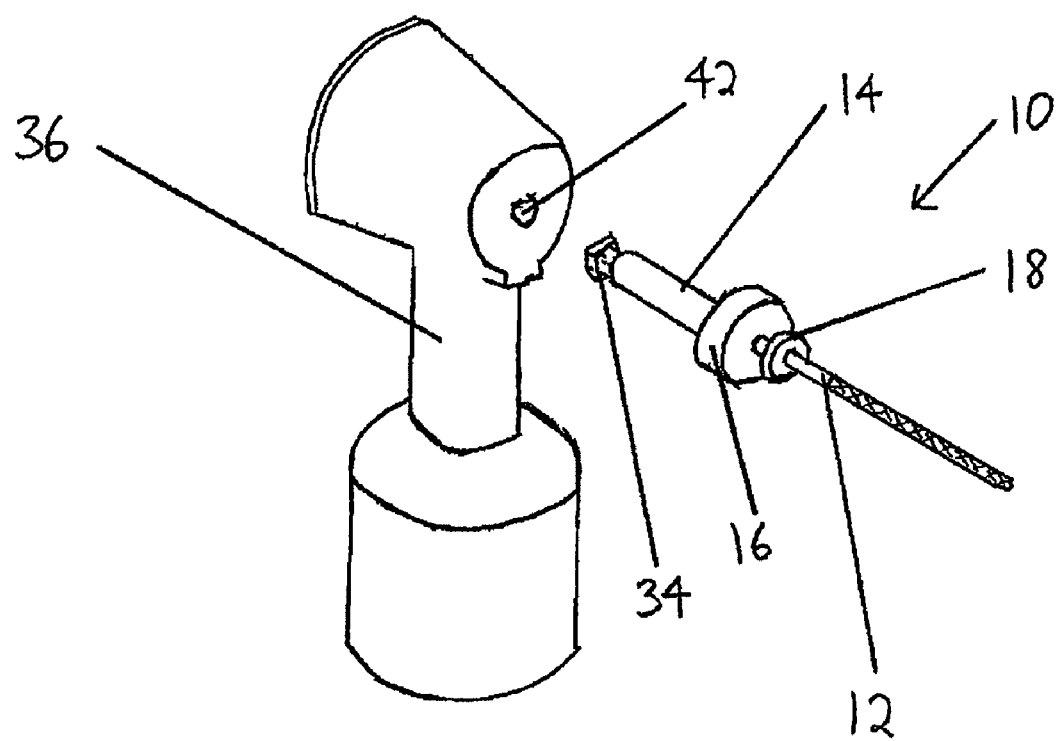
FIG. 3 shows a perspective view of the instrument of FIG. 1 relative to an example of a dental tool that may be used to rotate the instrument.
Figure 4:
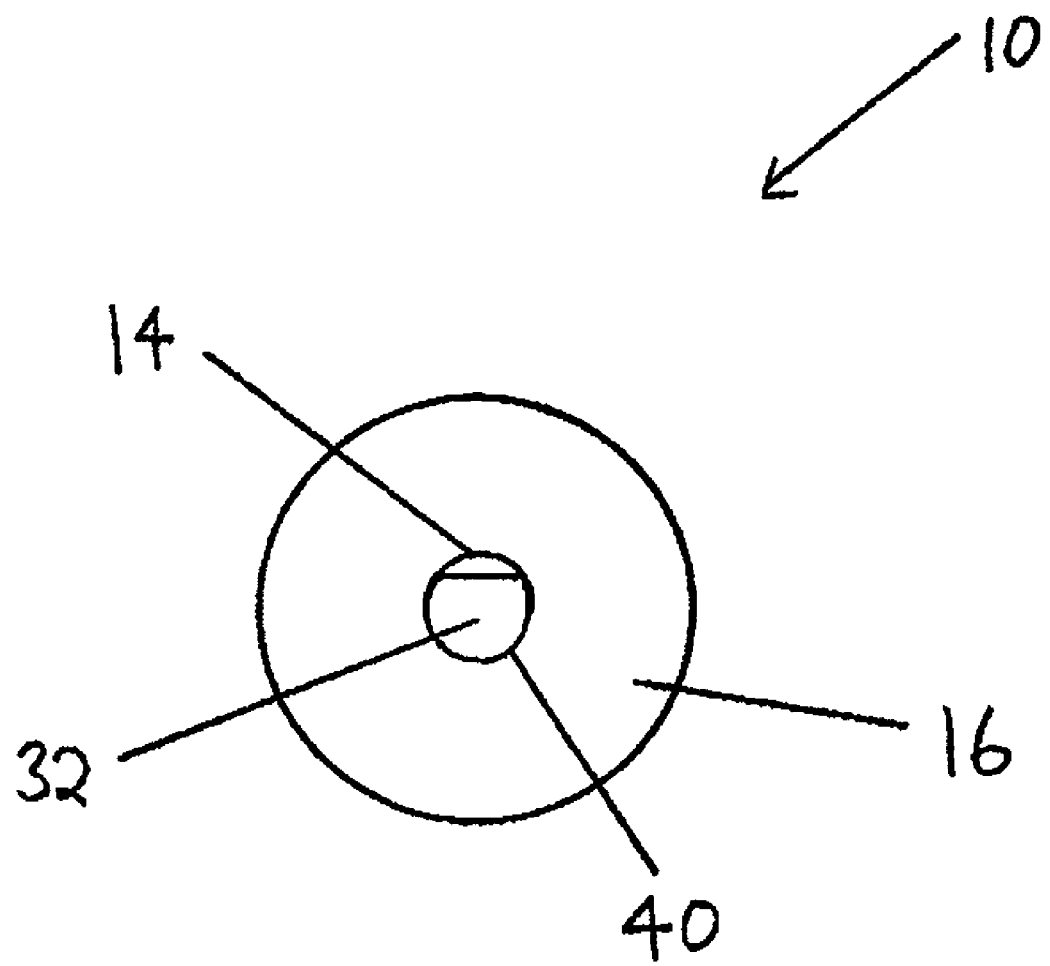
FIG. 4 shows an end view of the instrument of FIG. 1 or FIG. 2 in which a handle is visible.

The handle 14 includes a first end 30 and a second end 32. In a preferred embodiment, the handle 14 is made of stainless steel or nickel titanium (preferably about 55/45 by weight). However, in alternate embodiments, other suitable materials may be used for the handle. The length of the handle preferably ranges from about 10 millimeters (mm) to about 20 mm, although handles of other suitable lengths may be used. In a preferred embodiment as shown in FIGS. 1-3, the second end 32 of the handle 14 includes an attachment member 34 for removable attachment to a dental tool rotation device 36 or other similar device. The attachment member 34 shown in FIGS. 1-3 is preferably keyed to include, for example, a groove 38 and a nub 40. In one example, the nub 40 is shaped to be received by a port 42 on the dental tool rotation device 36 or other similar device. FIG. 4 shows a view from the second end 32 of the handle 14. Although the groove/nub attachment mechanism shown in FIGS. 1-4 is one preferred embodiment, other attachment mechanisms suitable for attaching the instrument to a hand-held device may be located on the second end of the handle or elsewhere on the endodontic instrument.

Figure 5:
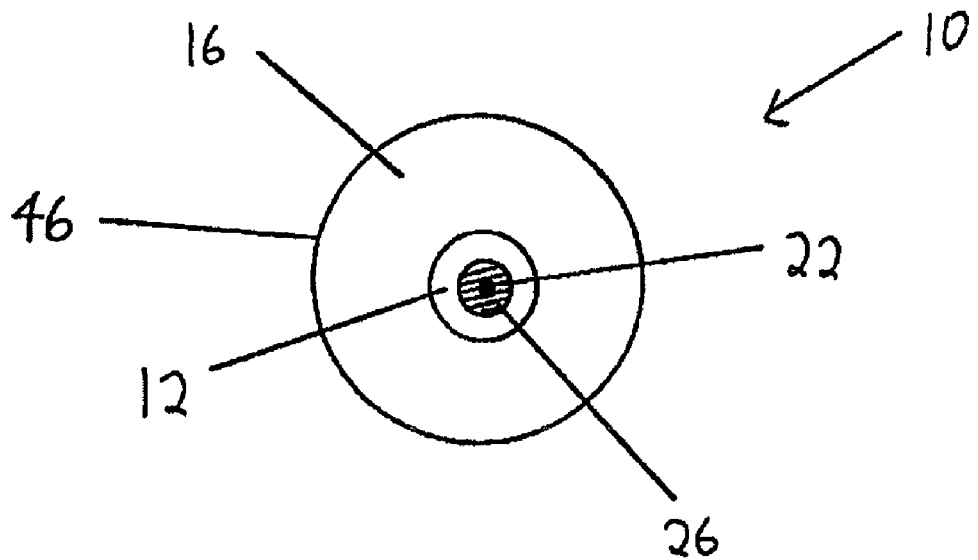
FIG. 5 shows an end view of the instrument of FIG. 1 in which a distal end of an elongate shaft is visible.
Figure 6:
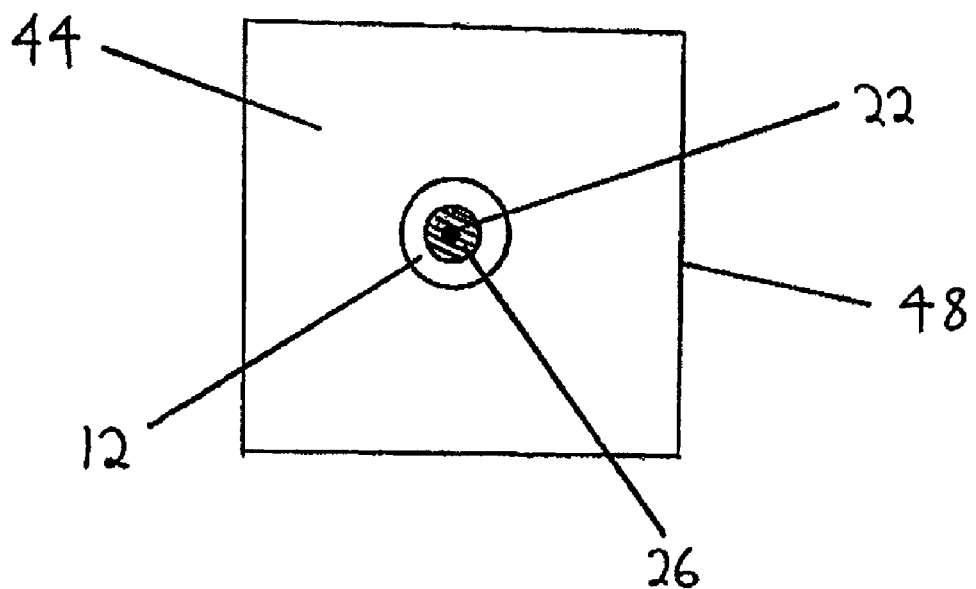
FIG. 6 shows an end view of an embodiment of an endodontic instrument similar to the instrument of FIG. 1 but including a different shaped projection.

A radially extending projection 16 preferably extends from adjacent the first end of the handle 14. However, in alternate embodiments, the projection may extend from a portion of the shaft 12 and may be separate from the handle 14. The projection 16 extends partially or completely around the perimeter of the instrument 10. The projection 16 is preferably made of the same material as the handle 14, but may be made of a different suitable material. The radially extending projection 16 is preferably not removable from the instrument and is in a fixed position on the handle or shaft. In various embodiments of the present invention, the projection 16 may have a variety of different cross-sectional shapes as shown by in FIG. 5 (showing a circular projection 16) and FIG. 6 (showing a square projection 44). Generally, the cross-sectional shape of the projection 16 may include polygons, ovals, circles, or combination cross-sections that include both curved and straight edges. The distance from the outside edge (46, 48) of the projection (16, 44) to the shaft 12 preferably ranges from about 2 mm to about 4 mm. The average thickness of the projection (16, 44) preferably ranges from about 1 mm to about 4 mm. The diameter of the projection preferably ranges from about 5 mm to about 8 mm, and more preferably from about 6 mm to about 7 mm. The diameter of the remaining portions of the handle preferably ranges from about 2 mm to about 4 mm, and more preferably from about 2.5 mm to about 3.5 mm.

The extending projection 16 provides a portion of the instrument 10 which has a sufficiently large diameter for a user to hold adjacent such user's thumb and fingers and manually manipulate, as a handle which is too narrow may be difficult for a user to properly grip and control with precision. Additionally, the projection 16 provides a safety barrier which limits a user's thumb and/or fingers from slipping onto the shaft of the instrument or into a patient's mouth during manual manipulation. The remaining portion of the handle is narrow enough to fit into a hand-held instrument. The configuration of the handle/projection and the attachment member allows the instrument of the present disclosure to have a portion of the handle sufficiently large diameter to be properly used in manual procedures and a portion with an attachment member that is sufficiently narrow to fit within a hand-held device.

The disclosure also includes embodiments of a method for removing material from an internal portion of a tooth using the instrument (10, 11). In one embodiment, the method includes a step 110 of manipulating the endodontic instrument so that material from an internal portion of a tooth is displaced. In a particular embodiment, the endodontic instrument (10, 11) may be manipulated using an automated handpiece such as dental rotation device 36 and then manipulated manually (i.e., without using any automated features of a handpiece). Manual manipulation is preferably performed after removing the handpiece from the endodontic instrument. The method is particularly helpful because the handpiece may be used to manipulate the endodontic instrument in larger areas inside a tooth, and manual operation may be used when the endodontic instrument has penetrated into narrow or more sensitive areas of the interior of a tooth. In a preferred embodiment, manipulation using a handpiece and manual manipulation are both performed without removing the endodontic instrument from the tooth being operated on between steps.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method for removing material from an internal portion of a tooth using an endodontic instrument, the method comprising the steps of:
   a. displacing material from an internal portion of the tooth by manipulating the endodontic instrument using an automated handpiece;
   b. displacing material from an internal portion of the tooth by manipulating the endodontic instrument manually; and
   c. removing the endodontic instrument from the handpiece prior to the step of manipulating the endodontic instrument manually, wherein the endodontic instrument is not removed from the tooth being operated on while the handpiece is being removed,
   wherein the endodontic instrument comprises an elongated shaft including a proximal end and a distal end; a cutting surface extending along a working portion of the elongate shaft; a handle attached adjacent the proximal end of the elongate shaft, the handle including a first end and a second end; a projection extending around a portion of the perimeter of the shaft substantially adjacent the first end of the handle, wherein the projection provides a barrier to prevent a user's fingers from moving beyond the handle directly onto the elongate shaft; and an attachment member adjacent the second end of the handle for removable attachment of the instrument to an automated rotary dental device.

2. The method of claim 1 wherein the endodontic instrument further comprises a file.

3. The method of claim 1 wherein the endodontic instrument further comprises a reamer.

4. The method of claim 1 wherein the endodontic instrument further comprises a broach.

5. The method of claim 1 wherein the endodontic instrument further comprising a movable stop located around the elongate shaft.

6. The method of claim 1 further comprising a step of filling an internal portion of a tooth with a substantially biologically inert substance.

* * * * *